United States Patent [19]

Visor et al.

[11] Patent Number: 5,273,885
[45] Date of Patent: Dec. 28, 1993

[54] CONJUGATES OF MONOPHENYL THYROID ANALOGS USEFUL IN ASSAYS

[75] Inventors: Jill M. Visor, Pacifica; Anthony Delizza, Sunnyvale; Edwin F. Ullman, Atherton, all of Calif.

[73] Assignee: Syntex (U.S.A.) Inc., Palo Alto, Calif.

[21] Appl. No.: 923,413

[22] Filed: Jul. 31, 1992

[51] Int. Cl.$^5$ .................. G01N 33/536; G01N 33/535; G01N 33/537

[52] U.S. Cl. .................. 435/7.93; 435/7.9; 435/975

[58] Field of Search .................. 435/7.9, 7.93, 975; 436/500

[56] References Cited

U.S. PATENT DOCUMENTS

| | | | |
|---|---|---|---|
| 3,817,837 | 6/1974 | Rubenstein et al. | 195/103.5 |
| 3,875,011 | 4/1975 | Rubenstein et al. | 195/99 |
| 3,911,096 | 10/1975 | Chopra | 424/1 |
| 3,928,553 | 12/1975 | Hollander | 424/1 |
| 4,018,883 | 4/1977 | Parslow | 424/1 |
| 4,040,907 | 8/1977 | Ullman et al. | 435/20 |
| 4,043,872 | 8/1977 | Blakemore et al. | 435/7.8 |
| 4,121,975 | 10/1978 | Ullman et al. | 195/99 |
| 4,171,244 | 10/1979 | Blakemore et al. | 436/500 |
| 4,399,121 | 8/1983 | Albarella et al. | 530/363 |
| 4,410,633 | 10/1983 | Hertl et al. | 436/500 |
| 4,847,195 | 7/1989 | Khanna et al. | 435/7.9 |

*Primary Examiner*—Mary E. Ceperley
*Attorney, Agent, or Firm*—Theodore J. Leitereg

[57] ABSTRACT

Methods employing thyroid analog conjugates to enzymes and to immunogenic carriers are provided, which find use in the determination of thyroid compounds normally in physiological fluids, such as serum. The immunogenic carrier conjugates are used to raise antibodies specific to thyroid compounds. The antibodies and enzyme conjugates are used in assays for thyroid compounds. The thyroid analogs are characterized by the presence of only one phenyl ring that contains a hydroxyl substituent and one or two substituents in an ortho relationship to the hydroxyl substituent on the phenyl ring wherein the phenyl ring is conjugated to an enzyme or an immunogenic carrier by a bond or a linking group. Kits for conducting the methods of the present invention are also disclosed.

55 Claims, No Drawings

CONJUGATES OF MONOPHENYL THYROID ANALOGS USEFUL IN ASSAYS

BACKGROUND OF THE INVENTION

1. Field of the Invention

Thyroxine is an important hormone in the mammalian physiology, being excreted by the thyroid gland. The measurement of thyroid hormones such as thyroxine is an important diagnostic tool in the determination of disease such as hypothyroidism and hyperthyroidism. Furthermore, monitoring of thyroid hormone levels in patients receiving therapy for thyroid disease is commonly done. Various techniques have been used for the determination of thyroid hormones, including radioimmunoassay, competitive protein binding, chromatography, etc. These techniques suffer from a number of disadvantages in being difficult to carry out and in the case of radioimmunoassay having unstable reagents. Enzyme immunoassays such as homogeneous enzyme immunoassays have also been utilized for the determination of total thyroxine and serum thyroid protein binding capacity.

Use of complete thyroxine molecules as part of enzyme conjugates, such as conjugates of the complete thyroxine molecule with glucose-6-phosphate dehydrogenase (G-6-PDH), for competitive homogeneous enzyme immunoassays has resulted in several difficulties. In the first place the binding of antibody to the conjugates does not produce the requisite inhibition of enzyme activity necessary to achieve an adequate change of enzyme activity so that a sensitive assay is achieved. Secondly, the complete thyroxine molecule is bulky and has hydrophobic properties, which serve to destabilize an enzyme to which it is attached. In addition, G-6-PDH conjugates containing complete thyroxine molecules are very sensitive to binding of sample serum proteins, such as immunoglobulins, and are deactivated by such binding of serum proteins when it occurs in a certain small percentage of patient samples. The sample serum protein binding interference is inhibitory to the enzyme conjugate and negatively affects the performance of the immunoassay in terms of quantitation of the thyroid hormone analyte. The exact mechanism of the protein binding in such samples is not clear, but it may be a manifestation of autoimmune disorders in which antibodies to thyroxine-like molecules are present.

2. Description of the Related Art

U.S. Pat. No. 3,817,837 describes enzyme immunoassays. U.S. Pat. No. 4,040,907 discloses iodothyronine enzyme conjugates. U.S. Pat. No. 4,171,244 discloses enzyme-bound-polyiodothyronine. A polyiodothyronine immunoassay is described in U.S. Pat. No. 4,043,872. U.S. Pat. No. 4,121,975 teaches a pretreatment of samples for polyiodothyronine assays. Enzyme immunoassays with glucose-6-phosphate dehydrogenase are described in U.S. Pat. No. 3,875,011. A method for the measurement of free thyroxine or 3,5,3'-triiodothyronine in a liquid sample is described in U.S. Pat. No. 4,410,633. Iodothyronine immunogens and antibodies are taught in U.S. Pat. No. 4,399,121. A thyroxine radioimmunoassay is described in U.S. Pat. No. 4,018,883. A radioimmunoassay for measurement of thyroxine and triiodothyronine in blood serum is disclosed in U.S. Pat. No. 3,911,096. A radioimmunoassay method for triiodothyronine and thyroxine is taught in U.S. Pat. No. 3,928,553. U.S. Pat. No. 4,847,195 discloses glucose-6-phosphate dehydrogenase conjugates useful in polyiodothyronine assays.

SUMMARY OF THE INVENTION

The present invention concerns methods for analyzing for the presence or amount of a thyroid compound in a medium suspected of containing a thyroid compound. The method comprises the steps of (a) combining the medium with an antibody specific for the thyroid compound and an enzyme conjugate comprising an enzyme bound to a thyroid analog and (b) determining the effect of the assay medium on the activity of the enzyme. The improvement of the present invention comprises the thyroid analog being a compound having only one phenyl ring that contains a hydroxyl substituent and one or two additional substituents in an ortho relationship to the hydroxyl substituent on the phenyl ring.

Another improvement in accordance with the present invention comprises the antibody being raised against an immunogenic conjugate comprising an immunogenic carrier bound to a thyroid analog. The thyroid analog has only one phenyl ring that contains a hydroxyl substituent and one or two iodine atoms in an ortho relationship to the hydroxyl substituent on the phenyl ring.

In one embodiment of the methods of the present invention a compound of the following formula is employed:

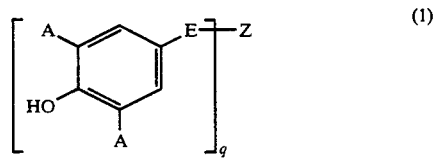

wherein:

A is independently iodine, t-butyl or hydrogen, preferably iodine or hydrogen, wherein at least one of A is other than hydrogen.

E is a bond or a linking group having a chain having a length of 1 to 1? atoms, said atoms being selected from the group consisting of carbon, oxygen, nitrogen, sulfur and phosphorus, with the proviso that the atoms of the chain not include a phenyl ring within at least 2 atoms, preferably at least 4 atoms, more preferably at least 5 atoms, of the phenyl ring bearing the hydroxy group, and preferably the chain does not include a phenyl ring, Z is an enzyme, and q is a number from 1 to the molecular weight of Z divided by 5000.

In another embodiment of the methods of the present invention an antibody raised against a compound of the following formula is employed:

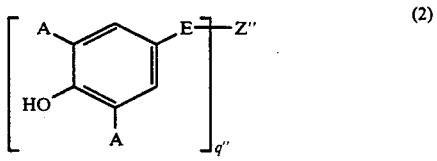

wherein:

A is independently iodine, t-butyl or hydrogen, preferably iodine or hydrogen, wherein at least one of A is other than hydrogen.

E is a bond or a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms, preferably at least 4 atoms, more preferably at least 5 atoms, of the phenyl ring bearing the hydroxy group, and preferably the chain does not include a phenyl ring, Z" is an immunogenic carrier, and q" is a number from 1 to the molecular weight of Z' divided by 5000.

In another embodiment of the present invention kits for conducting the present methods comprise in packaged combination (a) a compound of the above formula 1 and (b) an antibody specific for a thyroid compound.

Another aspect of the present invention concerns kits for conducting the present methods. The kits comprise in packaged combination (a) a conjugate of a thyroid analog and an enzyme and (b) an antibody raised against a compound of the above formula 2.

DESCRIPTION OF THE SPECIFIC EMBODIMENTS

The compounds employed in the present invention are thyroid analogs conjugated to enzymes or immunogenic carriers. For the enzyme conjugates the enzymatic activity is substantially decreased when bound to an antibody specific for a thyroid compound. The conjugates to immunogenic carriers are used to raise antibodies specific for thyroid compounds. The thyroid analogs are characterized by having only one phenyl ring that contains a hydroxyl substituent and one or two additional substituents, usually iodo or t-butyl preferably iodo, in an ortho relationship to the hydroxyl substituent on the phenyl ring. The thyroid analogs are conjugated to an enzyme or an immunogenic carrier by a bond or a linking group having a chain of one to ten atoms in length. The atoms in the chain are selected from the group consisting of carbon, oxygen, nitrogen, sulfur and phosphorus, with the proviso that the atoms of the chain not be part of a phenyl ring unless that phenyl ring is at least 2 atoms, preferably at least 4 atoms, more preferably at least 5 atoms, removed from the phenyl ring bearing the hydroxy substituent. Preferably, the atoms of the chain are not part of a phenyl ring.

Before proceeding further with the description of specific embodiments of the present invention, a number of terms will be defined.

Thyroid compound: polyiodothyronine compounds, which can be detected in an assay employing the conjugates of the present invention. For the most part the compounds have the following formula:

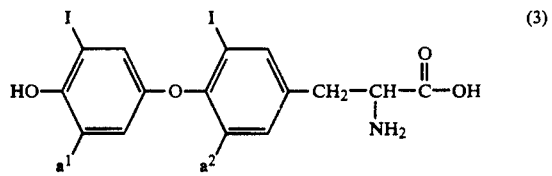

(3)

wherein $a^2$ and $a^1$ may both be iodine or one may be iodine and one hydrogen. As can be seen, these polyiodothyronine compounds have more than one phenyl ring having hydroxyl substituent or a substituted hydroxyl substituent, namely, the ether linkage, and one or more iodine atoms in an ortho relationship to the hydroxyl or substituted hydroxyl. Exemplary of such analytes are O-(4-hydroxy-3,5-diiodophenyl)-3,5-diiodotyrosine (3,5,3'5'-tetraiodothyronine, thyroxine or T4)and O-(4-hydroxy-3-iodophenyl)-3,5-diiodotyrosine (3,5,3'-triiodothyronine or T3), and 3',5',3-Triodothyronine (Reverse T3). The thyroid compound may be a molecule found directly in a sample such as a body fluid from a host. The sample can be examined directly or may be pretreated to render the thyroid compound more readily detectable. For example, the sample may be pretreated to free the thyroid compound from a naturally occurring receptor such as thyroxine binding globulin. Such pretreatment procedures are well-known in the art and are described in, for example, U.S. Pat. No. 4,121,975. Furthermore, the thyroid compound may be determined by detecting an agent probative of the thyroid compound such as a specific binding pair member complementary to the thyroid compound, whose presence will be detected only when the thyroid compound of interest is present in a sample. Thus, the agent probative of the thyroid compound becomes the analyte that is detected in an assay. The body fluid can be, for example, urine, blood, plasma, serum, saliva, semen, stool, sputum, cerebral spinal fluid, tears, mucus, and the like and is usually serum.

Thyroid analog: the thyroid analog significantly differs from the polyiodothyronine compounds in that the thyroid analog has only one phenyl ring that contains a hydroxyl substituent and one or two additional substituents in an ortho relationship to the hydroxyl substituent on the phenyl ring. Other phenyl rings may be present in the thyroid analog, for example, in the linking group, but must be a sufficient distance from the above phenyl ring so as to avoid the detrimental effects described above for conjugates of conventional thyroid molecules. Normally, the additional substituents are iodine although groups that are isosteric with iodine such as t-butyl serve as suitable iodine surrogates.

T-butyl: 1,1-dimethylethyl.

Member of a specific binding pair ("sbp member"): one of two different molecules, having an area on the surface or in a cavity which specifically binds to and is thereby defined as complementary with a particular spatial and polar organization of the other molecule. The members of the specific binding pair can be referred to as ligand and receptor (antiligand) such as when they are members of an immunological pair such as antigen-antibody. Other specific binding pairs, which are not immunological pairs, may also be used in an assay in accordance with this invention depending on the particular protocol chosen, for example, biotin-avidin, hormones-hormone receptors, nucleic acid duplexes, IgG-protein A, polynucleotide pairs such as DNA-DNA, DNA-RNA, and complementary enzyme fragments.

Receptor ("antiligand"): any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Antibody: an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Kohler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981). For example, a compound of structure 2 can be used as the immunogen. Samples of the immunogen preparations are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microliter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kohler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Specific binding: the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding: non-covalent binding between molecules that is relatively independent of specific surface structures. Such non-specific binding will usually result from charge or electronic interactions between oppositely charged molecules. Non-specific binding may also result from hydrophobic interactions between molecules.

Conjugate: a molecule comprised of two or more subunits bound together, optionally through a linking group, to form a single structure. The binding can be made either by a direct connection (e.g. a chemical bond) between the subunits or by use of a linking group. For example, in one context of the present invention, a thyroid analog conjugated, optionally through a linking group, to an enzyme, is a thyroid analog-enzyme conjugate.

Conjugation: any process wherein two subunits are linked together to form a conjugate. The conjugation process can be comprised of any number of steps.

Immunogenic carrier: a material for attachment to a thyroid analog thus rendering the thyroid analog immunogenic, that is, having the ability to elicit an immune response in a host to which the thyroid analog-immunogenic carrier is administered. One group of immunogenic carriers is the poly(amino acids) of molecular weight greater than 2000, preferably greater than 5000. Examples, by way of illustration and not limitation, of some common poly(amino acids) useful as immunogenic carriers are albumins, such as bovine serum albumin, and gammaglobulins, such as bovine gammaglobulin. Another group of immunogenic carriers are particles such as, by way of illustration and not limitation, bacteria, liposomes or polystyrene beads.

Linking group: the covalent linkage between the thyroid analog and the enzyme or the immunogenic carrier. Functional groups that are normally present or are introduced on an enzyme or an immunogenic carrier will be employed for linking these materials to a thyroid analog.

For the most part, carbonyl functionalities will find use, both oxocarbonyl, e.g., aldehyde; sulfonyl (derived from sulfonic acids); and non-oxocarbonyl (including nitrogen and sulfur analogs) e.g., carboxyl, amidine, amidate, thiocarboxy and thionocarboxy. As used herein, the term "non-oxo-carbonyl" shall include the carbonyl group of carboxylic acids, —COOH; the nitrogen containing iminocarbonyl group of amidic acids, —C(NH)OH; and the sulfur containing thionocarbonyl group of thio acids, —C(S)OH. Alternative functionalities of oxo include active halogen, diazo, mercapto, olefin, particularly activated olefin, amino, phosphoro and the like. A description of linking groups may be found in U.S. Pat. No. 3,817,837, the relevant disclosure of which is incorporated herein by reference.

The linking group contains a chain of from 1 to 10 atoms, usually from about 2 to 8 atoms, preferably 4 to 7 atoms, each independently selected from the group normally consisting of carbon, oxygen, nitrogen, sulfur and phosphorous with the proviso that the atoms of the chain not be part of a phenyl ring unless such phenyl ring is at least 2 atoms, preferably at least 4 atoms, more preferably at least 5 atoms, from the phenyl ring bearing the hydroxy substituent. Preferably, the atoms of the chain are not part of a phenyl ring. The number of heteroatoms in the linking group will normally range from about 0 to 4, usually from about 1 to 2. Common functionalities in forming a covalent bond between the linking group and the molecule to be conjugated are carboxamides, thiocarboxamides, carbamates, thiocarbamates, carboxylic acid esters, thioesters, sulfonic acid esters, phosphoric acid esters, ureas, thioureas, carbamates, phosphoramides, sulfonamides, ethers, sulfides, thioethers, olefins, acetylenes, amines, amidines, amides, thioamides, ketones, and the like. The chain of the linking group can contain more than one of the above functionalities, usually one to two of the above functionalities.

The atoms in the chain may be substituted with atoms other than hydrogen. Generally, the predominant atom as a substituent is hydrogen (H) but may also be halogen (chlorine, bromine and fluorine), oxygen (O), nitrogen (N), sulfur (S), phosphorus (P), wherein the O, N, S, or P, if present, are bound to carbon or one or more of each other or to hydrogen to form various functional groups, such as, for example, carboxylic acids, alcohols, thiols, carboxamides, carbamates, carboxylic acid esters, thioesters, sulfonic acids, sulfonic acid esters, phosphoric acids, phosphoric acid esters, ureas, thioureas, carbamates, phosphoramides, sulfonamides, ethers, sulfides, thioethers, olefins, acetylenes, amines, amidines, amides, thioamides, ketones, aldehydes, nitriles, and the like. Illustrative of such organic radicals or groups, by way of illustration and not limitation, are alkyl, alkylidine, aryl, aralkyl, and alkyl, aryl, and aralkyl substituted with one or more of the aforementioned functionalities. Generally, when heteroatoms are present, oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Ancillary Materials: Various ancillary materials will frequently be employed in an assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially: when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Enzyme: Exemplary of enzymes that may be utilized in the present invention are:

| NAME & CLASS | DISTRIBUTION | SUBSTRATE | END-PRODUCTS |
|---|---|---|---|
| Hydrolases | | | |
| Carbohydrases | | Carbohydrates | |
| 1. Amylase | Pancreas, saliva malt, etc. | Starch, dextrin, etc. | Maltose and dextrins |
| 2. Lactase | Intestinal juice, mucosa | Lactose | Glucose and galactose |
| 3. Maltase | Intestinal juice, yeast, etc. | Maltose | Glucose |
| 4. Sucrase | Intestinal juice, yeast, etc. | Sucrose | Glucose and fructose |
| 5. Emulsin | Plants | β-Glucosides | Glucose, etc. |
| Nucleases | | Nucleic acid & derivatives | |
| 1. Polynucleotidase | Pancreatic juice, intestinal juice, etc. | Nucleic acid | Nucleotides |
| 2. Nucleotidase | Intestinal juice and other tissues | Nucleotides | Nucleotides and phosphoric acid |
| 3. Nucleotidase | Animal tissues | Nucleotides | Carbohydrate and bases |
| Amidases | | Amino compounds and amides | |
| 1. Arginase | Liver | Arginine | Ornithine and urea |
| 2. Urease | Bacteria, soybean, jack bean, etc. | Urea | Carbon dioxide ammonia |
| 3. Glutaminase | Liver, etc. | Glutamine | Glutamic acid and ammonia |
| 4. Transaminase | Animal tissues | Glutamic acid and oxalacetic acid, etc. | α-Ketoglutaric acid, aspartic acid, etc. |
| Purine Deaminases | | Purine bases & derivatives | |

| NAME & CLASS | DISTRIBUTION | SUBSTRATE | END-PRODUCTS |
|---|---|---|---|
| 1. Adenase | Animal tissues | Adenine | Hypoxanthine and ammonia |
| 2. Guanase | Animal tissues | Guanine | Xanthine and ammonia |
| Pentidases | | Peptides | |
| 1. Aminopolypeptidase | Yeast, intestines etc. | Polypeptides | Simpler peptides and amino acids |
| 2. Carboxypep- | Pancreas | Polypeptides | Simpler peptides peptides and amino acids |
| 3. Dipeptidase | Plant and animal tissue and bacteria | Dipeptides | Amino acids |
| 4. Prolinase | Animal tissues and yeast | Proline peptides | Proline and simpler peptides |
| uz,3/9 Proteinases | | Proteins | |
| 1. Pepsin | Gastric juice | Proteins | Proteoses, peptones, etc. |
| 2. Trypsin | Pancreatic juice | Proteins, proteoses, and peptones | Polypeptides and amino acids |
| 3. Cathepsin | Animal tissues | Proteins | Proteoses and peptones |
| 4. Rennin | Calf stomach | Casein | Paracasein |
| 5. Chymotrypsin | Pancreatic juice | Proteins, proteoses, and peptones | Polypeptides and amino acids |
| 6. Papain | Papaya, other plants | Proteins, proteoses, and peptones | |
| 7. Ficin | Fig sap | Proteins | Proteoses, etc. |
| Esterases | | Esters | Alcohols and acids |
| 1. Lipase | Pancreas, castor bean, etc. | Fats | Glycerol and fatty acids |
| 2. Esterases | Liver, etc. | Ethyl butyrate, etc. | Alcohols and acids |
| 3. Phosphatases | Plant and animal tissues | Esters of phosphoric acid | Phosphate and alcohol |
| 4. Sulfatases | Animal and plant tissues | Esters of sulfuric acid | Sulfuric acid and alcohol |
| 5. Cholinesterase | Blood, tissues | Acetylcholine | Choline and acetic acid |
| Iron Enzymes | | | |
| 1. Catalase | All living organisms except a few species of microorganisms | Hydrogen peroxide | Water and oxygen |
| 2. Cytochrome | All living organisms except a few species of microorganisms | Reduced cytochrome C in the presence of oxygen | Oxidized cytochrome C and |
| 3. Peroxidase | Nearly all plant cells | A large number of phenols, aromatic amines, etc. in the presence of $H_2O_2$ | Oxidation product of substrate and water |
| Copper Enzymes | | | |
| 1. Tyrosinase (poly-phenoloxidase, monophenoloxidase) | Plant and animal tissues | Various phenolic compounds | Oxidation product of substrate |
| 2. Ascorbic acid oxidase | Plant tissues | Ascorbic acid in the presence of oxygen | Dehydroascorbic acid |
| Enzymes Containing Coenzymes I and/or II | | | |
| 1. Alcohol dehydrogenase | Animal and plant tissues | Ethyl alcohol and hols | Acetaldehyde and other aldehydes |
| 2. Malic dehydrogenase | Animal and plant tissues | L() Malic acid | Oxalacetic acid |
| 3. Isocitric hydrogenase | Animal and plant tissue | L-Isocitric acid acid | Oxalosuccinic acid |
| 4. Lactic dehydrogenase | Animal tissues and yeast | Lactic acid | Pyruvic acid |
| 5. β-Hydroxybutyric | Liver, kidneys, and heart | L-β-Hydroxybutyric acid | Acetoacetic acid |

-continued

| NAME & CLASS | DISTRIBUTION | SUBSTRATE | END-PRODUCTS |
|---|---|---|---|
| dehydrogenase | | | |
| 6. Glucose dehydrogenase | Animal tissues | D-Glucose | D-Gluconic acid |
| 7. Robison ester dehydrogenase | Erythrocytes and yeast | Robison ester (hexose-6-phosphate | Phosphohexonic |
| 8. Glycerophosphate dehydrogenase | Animal tissues | Glycerophosphate | Phosphoglceril acid |
| 9. Aldehyde dehydrogenase | Liver | Aldehydes | Acids |
| Enzymes which Reduce Cytochrome | | | |
| 1. Succinic dehydrogenase (as ordinarily prepared) | Plants, animals and microorganisms | Succinic acid | Fumaric acid |
| Yellow Enzymes | | | |
| 1. Warburg's old yellow enzyme | Yeast | Reduced co-enzyme II | Oxidized co-enzyme II and reduced yellow enzyme |
| 2. Diaphorase | Bacteria, yeasts higher plants and animals | Reduced co-enzyme I | Oxidized co-enzyme I and reduced yellow diaphorase |
| 3. Haas enzyme | Yeast | Reduced co-enzyme II | Oxidized co-enzyme II and reduced yellow enzyme |
| 4. Xanthine oxidase | Animal tissues | Hypoxanthine xanthine, aldehydes, reduced coenzyme I, etc. | Xanthine, uric acid, acids, oxidized co-enzyme I, etc. In presence of air, $H_2O_2$ |
| 5. D-amino acid oxidase | Animal tissues | D-Amino acids + $O_2$ | a-Keto-acids + $NH_3$, + $H_2O_2$ |
| 6. L-Amino oxidases | Animals, snake venoms | L-Amino acids | Keto acids, ammonia |
| 7. TPN-Cytochrome C reductase | Yeast, liver | Reduced co-enzyme II and cytochrome C | Oxidized co-enzyme I and reduced cytochrome C |
| 8. DPN Cytochrome C reductase | Liver, yeast | Reduced co-enzyme I and cytochrome C | Oxidized co-enzyme I and reduced cytochrome C |
| Hydrases | | | |
| 1. Fumarase | Living organisms in general | Fumaric acid + $H_2O$ | L-Malic acid |
| 2. Aconitase | Animal and plants | Citric acid | cis-Aconitic acid and L-isocitric acid |
| 3. Enolase | Animal tissues and yeast | 2-Phosphoglyceric acid | Phospyruvic acid + $H_2O$ |
| Mutases | | | |
| 1. Glyoxalase | Living organisms in general | Methyl glyoxal and other substituted glyoxals | D(−) Lactic acid |
| Desmolases | | | |
| 1. Zymohexase (aldolase) | All cells | Fructose-1,6-diphosphate | Dihydroxy-acetone phosphoric acid and phosphoglyceric acid |
| 2. Carboxylase | Plant tissues | Pyruvic acid | Acetaldehyde and $CO_2$ |
| 3. β-Keto-carboxylases | Animals, bacteria, plants | β-Keroacids | a-Keto acids |
| 4. Amino acid deoarboxylases | Plants, animals, bacteria | L-Amino acids | Amines and $CO_2$ |
| 5. Carbonic anhydrase | Erythrocytes | Carbonic acid | $CO_2$ + $H_2O$ |
| Other Enzymes | | | |
| 1. Phosphorylase | Animal and plant tissues | Starch or glycogen | Glucose-1-phosphate and phosphate |
| 2. Phosphohexo-isomerase | Animal and plant tissues | Glucose-6-phosphate | Fructose-6-phosphate |

-continued

| NAME & CLASS | DISTRIBUTION | SUBSTRATE | END-PRODUCTS |
|---|---|---|---|
| 3. Hexokinase | Yeast, animal tissues | Adenosine-triphosphate | Adenosine-diphosphate + glucose-6-phosphate |
| 4. Phosphoglucomutase | Plant and animals | Glucose-1-phosphate | Glucose-6-phosphate |

Of the various enzymes, the following table indicates enzymes of particular interest set forth in accordance with the I.U.B. classification.

1. Oxidoreductases 1.1 Acting on the CH-OH group of donors 1.1.1 With NAD+ or NADP+ as acceptor
1. alcohol dehydrogenase
6. glycerol dehydrogenase
17. mannitol-1-phosphate dehydrogenase
26. glyoxylate reductase
27. lactate dehydrogenase
37. malate dehydrogenase
49. glucose-6-phosphate dehydrogenase
1.1.2 With a cytochrome as an acceptor
3. lactate dehydrogenase (cytochrome)
1.1.3 With $O_2$ as acceptor
4. glucose oxidase
9. galactose oxidase 1.4 Acting on the $CH-NH_2$ group of donors 1.4.3 With $O_2$ as acceptor
2. L-aminoacid oxidase
3. D-aminoacid oxidase 1.6 Acting on NADH or NADPH 1.6.99 With other acceptors diaphorase 1.10 Acting on diphenols and related substances as donors 1.10.3 With $O_2$ as acceptor
1. catechol oxidase
3. ascorbate oxidase 1.11 Acting on $H_2O_2$ as acceptor 1.11.1 NAD+ peroxidase
6. catalase
7. peroxidase 3. Hydrolases 3.1 Acting on ester bonds 3.1.1 Carboxylic ester hydrolases
8. cholinesterase
3.1.3 Phosphoric monoester hydrolases
1. alkaline phosphatase
3.1.4 Phosphoric diester hydrolases
3. phospholipase C 3.2 Acting on glycosyl compounds 3.2.1 Hydrolysing O-glycosyl compounds
1. α-amylase
4. cellulase
17. lysozyme
23. β-D-galactosidase
31. β-D-glucuronidase 3.4 Acting on peptide bonds 3,4.17 Metallo-carboxypeptidases
1. carboxypeptidase A
3.4.21 Serine proteinases
5. α-chymotrypsin
3.4.22 Thiol proteinases
2. papain 3.5 Acting on C-N bonds, other than peptide bonds 3.5.1 In linear amides
5. urease 3.6 Acting on acid anhydride bonds 3.6.1 In phosphoryl-containing anhydrides
1. inorganic pyrophosphatase 4. Lyases 4.1 Carbon-carbon lyases
4.1.2 Aldehyde-lyases
4.2 Carbon-oxygen lyases
4.2.1 Hydro-lases
1. carbonate dehydratase 4.3 Carbon-nitrogen lyases 4.3.1 Ammonia-lyases
3. histidine ammonia-lyase In addition to whole enzymes, enzyme fragments may be used. Such enzyme fragments may themselves be active or later may be recombined with another enzyme fragment to produce active holoenzyme such as, for example, β-galactosidase fragments.

Enzymes of particular interest are oxidoreductases such as the dehydrogenases, for example, glucose-6-phosphatedehydrogenase (G6PDH) and malate dehydrogenase (MD).

The methods of the present invention preferably utilize thyroid analog-G6PDH conjugates. Glucose-6-phosphate dehydrogenase is an enzyme having the I.U.B. classification of oxidoreductase acting on the CH-OH group of donors having glucose-6-phosphate as a substrate. In general, any source or form of G6PDH can be used. However, it is especially preferred to select a microbial source which produces an enzyme which can use a cofactor that is not effective with G6PDH endogenous to a test sample, such as a mammalian body fluid. Microbial sources for G6PDH include *Leuconostoc mesenteriodes, Pseudomonas aeuroginosa, Hydrogenomonas H16, Thiobacillus ferrooxidans, Bacillus stearothermophilus, Bacillus mageratum, Zymomonas mobilis,* and the like. Particularly preferred are those G6PDH molecules that are able to utilize NAD. Since G6PDH from animal sources normally is able to utilize only NADP, one can limit interference from endogenous G6PDH by employing NAD as the cofactor, when enzyme conjugates are employed in immunoassays. G6PDH from *Leuconostoc mesenteriodes* and *Zymomonas mobilis* are particularly preferred for this reason.

Support or surface: a surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

The surface can have any one of a number of shapes, such as strip, rod, particle, including bead, and the like. The surface will usually be polyfunctional or be capable of being polyfunctionalized or be capable of binding an sbp member through specific, non-specific, covalent or non-covalent interactions. A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds, including the binding of sbp members to the support or surface, may be accomplished by well-known techniques, commonly available in the literature. See, for example, "Immobilized Enzymes," Ichiro Chibata, Halsted Press, New York (1978) and Cuatrecasas, J. Biol. Chem. 245:3059 (1970). The length of a linking group to the surface may vary widely, depending upon the nature of the compound being linked, the effect of the distance between the compound being linked and the surface on the specific binding properties and the like. An sbp member is normally bound to the outer surface of the support.

Signal Producing System ("sps"): the function of the signal producing system is to produce a product which provides a detectable signal related to the amount of bound and/or unbound enzyme. The sps may have one or more components, at least one component being an enzyme. The sps includes all of the reagents required to produce a measurable signal including signal producing means capable of interacting with the enzyme to produce a signal.

The signal producing system provides a signal detectable by external means, normally by measurement of electromagnetic radiation, desirably by visual examination. The signal producing system includes a chromophoric substrate and enzyme, where chromophoric substrates are enzymatically converted to dyes which absorb light in the ultraviolet or visible region, phosphors or fluorescers.

The signal producing means is capable of interacting with the enzyme label to produce a detectible signal. Such means include, for example, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The number of thyroid analogs conjugated to the enzyme will be at least 1, more usually at least 2, generally not exceeding 12, more usually not exceeding 10, and preferably within the range of about 3 to 8 on the average.

The enzyme conjugate will be capable of being employed in an immunoassay so that in combination with a receptor, preferably an antibody, and the unknown sample suspected of containing a thyroid compound, the amount of the thyroid compound in a sample suspected of containing the thyroid compound can be determined by comparison of the enzymatic activity of the assay sample compared to known standards.

For the most part, the thyroid analog-enzyme conjugates useful in the methods of the present invention have the following formula:

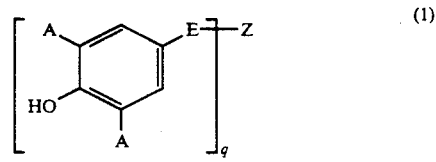

wherein:

A is independently iodine, t-butyl or hydrogen, preferably iodine or hydrogen, wherein at least one of A is other than hydrogen.

E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms, preferably at least 4 atoms, more preferably at least 5 atoms, of the phenyl ring bearing the hydroxy group, and preferably the chain does not include a phenyl ring, Z is an enzyme, and q is a number from 1 to the molecular weight of Z divided by 5000.

Preferably, the chain in the above conjugates is 2 to 8 atoms in length, where the atoms are selected from the group consisting of carbon, oxygen and nitrogen. More preferably, the chain in the above compound has the formula:

wherein R is independently selected from the group consisting of hydrogen, alkyl of 1 to 5 carbon atoms, $N(R')_2$ wherein R' are independently selected from the group consisting of hydrogen and alkyl of 1 to 5 carbon atoms, wherein one or more of the carbon atoms in R and/or R' may be substituted with carbon (C), chlorine, bromine, fluorine, oxygen (O), nitrogen (N), sulfur (S), or phosphorus (P), wherein the O, N, S, or P, if present, are bound to carbon or one or more of each other or to hydrogen to form a functional group, a is 0 or 1, b is 1 to 4, c is 1 or 2, d is 0 or 1, e is 1 or 2, f is 0 or 1 with the proviso that a+b+c+d+e not be greater than 7, and X is independently selected from the group consisting of oxygen, sulfur and NH.

More preferably, the chain in the above compound is independently selected from the group consisting of

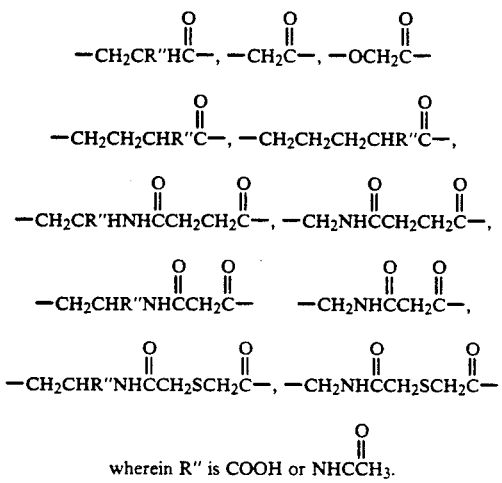

wherein R" is COOH or NHCCH$_3$.
                       ‖
                       O Some particularly useful compounds in the method of the present invention are compounds of the following formula:

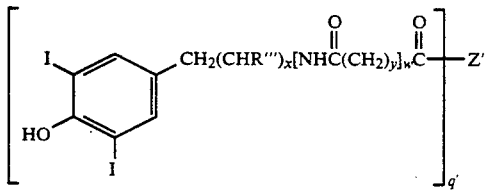

wherein:

R'" is selected from the group consisting of hydrogen, carboxy, carboxy alkyl ester of 1 to 5 carbon atoms and NHD', wherein D is selected from the group consisting of hydrogen and alkyl carbonyl (acyl) of 1 to 5 carbon atoms, Z' is glucose-6-phosphate dehydrogenase, q' is 1 to 10, and x is 0 or 1 y is 1 or 2 w is 0 or 1.

We have found that the thyroid analog-G6PDH conjugates when used in enzyme immunoassays provide distinct advantages over other polyiodothyronine-G6PDH conjugates having more than one phenyl ring that contains a hydroxyl substituent and one or two iodine atoms in an ortho relationship to the hydroxyl substituent on the phenyl ring. The conjugates of the present invention retain a substantial portion, about 30-60% of the original enzyme activity. The retained enzymatic activity can be inhibited by about 40-70% upon the binding to the conjugate to an antibody for a thyroid compound. Furthermore, thyroid analog-G6PDH conjugates used in the invention exhibit substantially reduced susceptibility to interference from samples that contain serum proteins when compared to that for previously used conjugates of polyiodothyronine compounds with G6PDH. In addition, the enzyme and immunogenic carrier conjugates used in the invention are less bulky and hydrophobic than previously used polyiodothyronine analog conjugates and, therefore, are more easily prepared and purified under mild conditions.

For the most part, polyclonal and monoclonal antibodies may be raised against thyroid analog-immunogenic carrier conjugates of the formula 2 and the antibodies obtained can be used in the methods of the present invention. Of course, polyclonal and monoclonal antibodies specific for a thyroid compound can be prepared using other immunogens and these antibodies can be utilized in the methods of the present invention as well. As mentioned above, the thyroid analog-immunogenic carrier conjugates of the invention have the following formula:

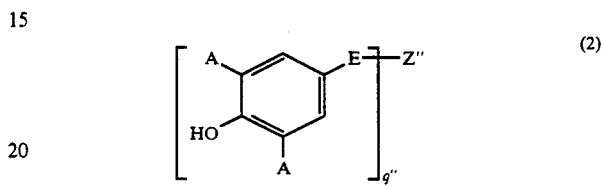

wherein:

A is independently iodine, t-butyl or hydrogen, preferably iodine or hydrogen, wherein at least one of A is other than hydrogen.

E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms, preferably at least 4 atoms, more preferably at least 5 atoms, of the phenyl ring bearing the hydroxy group, and preferably the chain does not include a phenyl ring, Z" is an immunogenic carrier, and q" is a number from 1 to the molecular weight of Z divided by 5000.

Preferably, the chain in the above compound is 2 to 8 atoms in length, where the atoms are selected from the group consisting of carbon, oxygen and nitrogen. More preferably, the chain in the above compound has the formula:

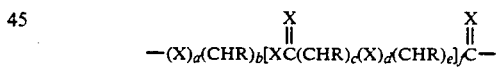

wherein R is independently selected from the group consisting of hydrogen, alkyl of 1 to 5 carbon atoms, N(R')$_2$ wherein R' are independently selected from the group consisting of hydrogen and alkyl of 1 to 5 carbon atoms, Wherein one or more of the carbon atoms may be substituted with carbon (C), chlorine, bromine, fluorine, oxygen (O), nitrogen (N), sulfur (S), phosphorus (P), wherein the O, N, S, or P, if present, are bound to carbon or one or more of each other or to hydrogen to form a functional group, a is 0 or 1, b is 1 or 4, c is 1 or 2, d is 0 or 1, e is 1 or 2, 0 or 1 f is 0 or 1 with the proviso that a+b+c+d+e not be greater than 7, and

X is independently selected from the group consisting of oxygen, sulfur and NH.

More preferably, the chain in the above compound is independently selected from the group consisting of

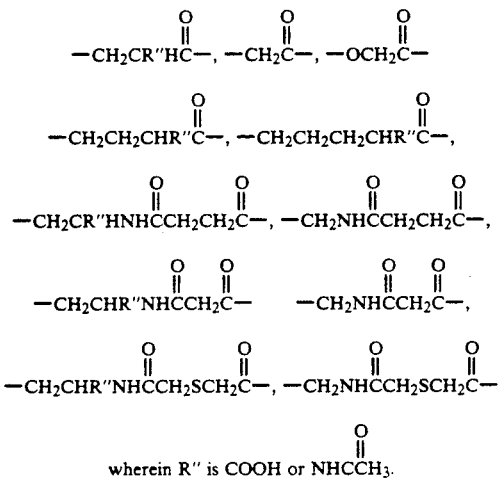

wherein R'' is COOH or NHCCH₃.
           ‖
           O

Some particularly useful immunogenic compounds useful in the methods of the present invention are compounds of the following formula:

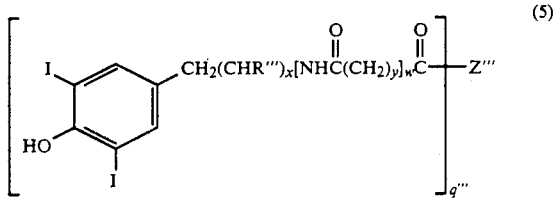

(5)

wherein:
R''' is selected from the group consisting of hydrogen, carboxy, carboxy alkyl ester of 1 to 5 carbon atoms and NHD', wherein D is selected from the group consisting of hydrogen and alkyl carbonyl (acyl) of 1 to 5 carbon atoms
Z''' is an albumin, a gammaglobulin or a keyhole limpet hemocyanin,
$q'''$ is 1 to 10,
x is 0 or 1'
y is 1 or 2 and
w is 0 or 1.

The thyroid analog-enzyme conjugates and/or the antibodies raised against the thyroid analog-immunogenic carrier conjugates can be used in a wide variety of immunoassays, either employing a separation step (heterogeneous assays) or not employing a separation step (homogeneous assays). These types of assays have been extensively described in the literature, for example, see "Enzyme-Immunoassay," by Edward T. Maggio, CRC Press, Inc., Boca Raton, Fla., 1980; U.S. Pat. Nos. 3,817,837 and 3,935,074 (the disclosures of which are incorporated herein by reference); which listing is not intended to be exhaustive.

For illustrative purposes, the following assay protocols are described wherein the analyte in the assay is thyroxine and the enzyme is G6PDH. This illustration should not be construed as a limitation on the scope of the invention.

In a heterogeneous assay, a thyroid analog-G6PDH conjugate, sample, and antithyroxine antibody bound to a surface or a support are combined in a suitable buffered medium. The mixture is incubated for a sufficient time, and the enzyme conjugate bound to antibody on the surface or support is separated from the unbound enzyme conjugate by any convenient means. For example, antibodies to anti-thyroxine can be bound to a microtiter well, which aids in a clean separation of the enzyme conjugate-anti-thyroxine complex from the assay medium. The assay medium or the surface or support is then examined for the enzyme activity of the remaining thyroid analog-G6PDH conjugate. In general, this examination involves the addition of other members of the signal producing system as described above. As described below, the enzyme activity is compared with the enzyme activity obtained using standards containing known amounts of thyroxine run in the same manner.

In a homogeneous assay, a thyroid analog-G6PDH conjugate, anti-thyroxine antibody and sample are combined and the combination is incubated for a sufficient time to provide for binding of antibody to thyroxine if present in the sample and to the thyroid analog - G6PDH conjugate. The enzyme activity in the solution is determined without separation and compared to the enzyme activity obtained with standards.

As mentioned above, the amount of thyroxine in the sample is determined by comparing the results of the assay to known standards or calibrators. For example, samples having known amounts of thyroxine are prepared, the assay carried out, and the enzymatic activity determined. The enzymatic activity is then graphed against the thyroxine concentration and the graph used to determine the amount of thyroxine in an unknown.

The conditions for the assay will vary depending upon the particular method employed. Where a homogeneous technique is used, the conditions will be selected so as to optimize the change in activity of the enzyme conjugate upon binding by the receptor. Normally, the pH will be in the range of about 5.5 to 10, more usually in the range of about 7 to 9.5, where strong binding between receptor and thyroxine occurs. Moderate temperatures will be employed, normally in the range of about 0° to 45°, more usually about 20° to 40° C.

The buffer solution employed will normally be at a concentration to provide in the assay medium a concentration of from about 0.001 to 0.5M, usually from about 0.01 to 0.2M. Protein will frequently be included to stabilize the enzyme; the protein can be an albumin, such as rabbit serum albumin, and/or gelatin, and will generally be present in about 0.005 to 0.5 weight percent in the final assay mixture, more usually from about 0.01 to 0.2 weight percent. Other additives may be present as found desirable, such as glycerol, Thimerosal, sodium azide, etc.

Concentration of the thyroid analog-enzyme conjugate will vary widely, depending on the concentration of thyroid compound of interest. Normally, the thyroid analog-enzyme conjugate concentration will be from about $10^{-5}$ to $10^{-13}$ M, more usually from about $10^{-7}$ to $10^{-11}$M. The ratio of binding sites to the concentration of conjugated thyroid analog will generally be at least about 0.5 and not greater than 1000, more usually being about from 1 to 100.

The order of addition of the reagents is not critical and the reagents and the sample can be combined simultaneously or wholly or partially sequentially. However, it is preferred that the thyroid analog-enzyme conjugate and receptor not be combined prior to the addition of the sample. The preferred order of addition is the sample and antibody, followed by the addition of thyroid analog-enzyme conjugate. The particular substrates for the enzyme that comprise the remainder of the signal producing system may be added at any convenient time. After each step the assay mixture may be incubated. Usually, incubation periods will be from about 10 seconds to 1 hour.

Enzyme activity determinations can be carried out for a duration of from about 5 seconds to 60 minutes, more usually being from about 0.25 to 30 minutes. For the most part, spectrophotometric techniques will be employed. However, other techniques include fluorimetry, titrimetry, etc.

The thyroid analog-enzyme conjugates and thyroid analog-immunogenic carrier conjugates can be prepared by techniques similar to those described in the literature. Compounds that may be utilized as the thyroid analogs are commercially available from, for example, Sigma Chemical Company, Pfalz and Bauer, Fluka, Aldrich Chemical Company, Lancaster and Janssen. The thyroid analogs can also be prepared by iodination of commercially available mono-(4-hydroxyphenyl) alkanoic acid compounds (1 to 5 carbon atoms) such as 3-(4-hydroxyphenyl)propionic acid and diiodotyrosine. The iodination is carried out according to well-known procedures such as that described in Bolton, et al., *Biochem. J.* (1973)133,529–539, the relevant disclosure of which is incorporated herein by reference.

The t-butyl derivatives can be prepared from the corresponding t-butyl phenol substituted alkanoic acids, some of which are commercially available and others of which can be synthesized according to known procedures. For example, 3,5-di-t-butyl-4-hydroxybenzoic acid is available from Aldrich Chemical Company. The synthesis of 3-t-butyl-4-hydroxybenzenepropanoic acid is described in European Patent Application EP 335,262. The synthesis of 3,5-di-t-butyl-4-hydroxyphenylacetic acid is described, for example, by Rieker, et al., *Tetrahedron* (1968) 24:103-112. The synthesis of 3-t-butyl-4-hydroxybenzoic acid is described, for example, by Hewgill (1978) 31:907-916.

Conjugation of proteins such as enzymes to low molecular weight compounds is described in, for example, U.S. Pat. No. 4,040,907, the relevant disclosure of which is incorporated herein by reference. For example, a non-oxo-carbonyl group, e.g., carboxyl group, on the thyroid analog can be activated for reaction with amine groups on the enzyme by formation of an ester with N-hydroxysuccinimide. Alternatively, a bromoacetyl derivative of the enzyme can be prepared, which can be reacted with an activated carboxylic acid on the thyroid analog in a manner similar to that described in U.S. Pat. Nos. 4,220,722 and 4,328,311.

Another aspect of the present invention relates to kits useful for conveniently performing an assay method of the invention for determining the presence or amount of an thyroid compound in a sample suspected of containing the thyroid compound. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises in packaged combination (a) a compound of the formula:

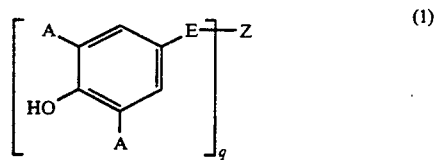

wherein:

A is independently iodine, t-butyl or hydrogen, preferably iodine or hydrogen, where at least one of A is other than hydrogen.

E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms, preferably at least 4 atoms, more preferably at least 5 atoms, of the phenyl ring bearing the hydroxy group, and preferably the chain does not include a phenyl ring, Z is an enzyme, and q is a number from 1 to the molecular weight of Z divided by 5000, and (b) an antibody specific for a thyroid compound.

Alternatively, the kit comprises in packaged combination (a) an antibody raised against a compound of the formula:

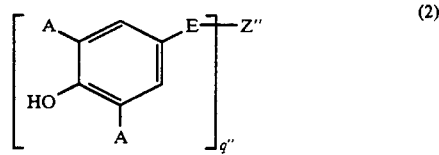

wherein:

A is independently iodine, t-butyl or hydrogen, preferably iodine or hydrogen, wherein at least one of A is other than hydrogen.

E is a bond or a linking group having a chain having a length of 1 to 10 atoms other than hydrogen, said atoms being selected from the group consisting of carbon, oxygen, nitrogen, sulfur and phosphorus, with the proviso that the atoms of said chain not include a phenyl ring within at least 2 atoms, preferably at least 4 atoms, more preferably at least 5 atoms, of the phenyl ring bearing the hydroxy group, and preferably the chain does not include a phenyl ring, Z" is an immunogenic carrier, and q" is a number from 1 to the molecular weight of Z divided by 5000, and (b) a conjugate of a thyroid analog and an enzyme. The antibody can be attached to a surface or a support. The kit can further include other separately packaged reagents for conducting an assay including ancillary reagents, and so forth.

EXAMPLES

The invention is demonstrated further by the following illustrative examples. Parts and percentages used herein are by weight unless otherwise specified. Temperatures are in degrees centigrade (°C.).

CONJUGATES OF THE EXAMPLES:

| EXAMPLE | CONJUGATE |
|---|---|
| 1 | 3,5-diiodo-4-hydroxyphenyl–CH$_2$CH$_2$C(=O)–NH–G6PDH (6) |
| 2 | 3,5-diiodo-4-hydroxyphenyl–CH$_2$C(=O)–NH–G6PDH (7) |
| 3 | 3,5-diiodo-4-hydroxyphenyl–CH$_2$CH$_2$NH–C(=O)–CH$_2$CH$_2$–C(=O)–NH–G6PDH (8) |
| 4 | 3,5-diiodo-4-hydroxyphenyl–CH$_2$CH(CO$_2$CH$_3$)NH–C(=O)CH$_2$CH$_2$C(=O)–NH–G6PDH (9) |
| 5 | 3,5-diiodo-4-hydroxyphenyl–CH$_2$CH(NHC(=O)CH$_3$)–C(=O)–NH–G6PDH (10) |
| 6 | 3,5-diiodo-4-hydroxyphenyl–OCH$_2$C(=O)NH–G6PDH (11) |
| 7 | 3,5-diiodo-4-hydroxyphenyl–CH$_2$–CH(CO$_2$H)–NH–C(=O)–CH$_2$S–CH$_2$C(=O)NH–G6PDH (12) |
| 8 | 3,5-diiodo-4-hydroxyphenyl–CH$_2$–CH(CO$_2$CH$_3$)–NH–C(=O)–CH$_2$S–CH$_2$C(=O)NH–G6PDH (13) |

EXAMPLE 1

Preparation of 3,5-diiodo-4-hydroxyphenylpropionic Acid and Conjugation to G6PDH To 3-(4-hydroxyphenyl)propionic acid (0.5 g) dissolved in 70% ethylamine (9.8 mL) and distilled water (19.6 mL) at 0° C., 2.0M I$_2$ in 2.5M KI (3.38 mL) was added slowly with stirring over 15 minutes. After stirring 2 hours at room temperature, 6N HCl was added to the chilled (0° C.) reaction mixture until pH 2-3. The white precipitate (3,5-diiodo 4-hydroxypropionic acid, DIHPA) was filtered and washed with distilled water.

The N-hydroxysuccinimide (NHS) ester of DIHPA was prepared using 1-(3-dimethylaminopropyl)-3-ethylcarbodiimide (EDCI). DIHPA (5 mg) and NHS (1.5 mg) were stirred at 4° C. to dissolution in 250 μl DMF. EDCI (2.5 mg) was added and the mixture stirred overnight at 4° C.

Native G6PDH was dialyzed at 4° C. with 3 changes of buffer (55 mM Tris, pH8). The concentration of enzyme used was 8-12 mg/mL. Dimethylformamide (DMF) was added to the chilled (4° C.) enzyme solution slowly to a 20% (v/v) ratio. The NHS ester solution was added slowly in portions to achieve appropriate % deactivation and % inhibition (% deactivation and % inhibition were determined by performing an enzyme activity determination on a known concentration of enzyme solution at each time point with T4 antibody present for determining percent inhibition and without T4 antibody present for determining percent activation). The resultant conjugate was dialyzed with 3 changes of buffer (1 & 2; 55 mM Tris, pH8 and 3; 50 mM phosphate, 150 mM NaCl pH7).

EXAMPLE 2

Preparation of 3,5-Diiodo-4-hydroxyphenylacetic Acid and Conjugation to G6PDH

Synthesis, NHS ester activation, and conjugation to G6PDH were carried out by a procedure similar to that of Example 1, starting from 3-(4-hydroxyphenyl)acetic acid.

EXAMPLE 3

Preparation of N-Succinamidoiiodotyramine and Conjugation to G6PDH

Tyramine, (Sigma Chemical Company), was iodinated to give diiodotyramine in a manner similar to that described in Example 1. To diiodotyramine (0.05 g) in pyridine (10 mL), succinic anhydride (0.0154 g) was added with stirring at room temperature. The reaction mixture cleared gradually with product formation over a period of 2 hours. The reaction was stirred an additional 2 hours at room temperature. Following solvent removal in vacuo, the product, N-succinamidodiiodotyramine, was purified by extraction (ethyl acetate (EtOAc):0.01N HCl), and preparative thin layer chromatography (TLC) (89:10:1 methylene chloride:methanol:trifluoroacetic acid) of the concentrated (in vacuo) EtOAc phases.

NHS ester activation and conjugation to G6PDH were carried out by a procedure similar to that described in Example 1.

EXAMPLE 4

Preparation of N-Succinamidodiiodotyrosine Methyl Ester and Conjugation to G6PDH To a vigorously stirring diiodotyrosine (Sigma Chemical Company) slurry (1 g) in anhydrous methanol (MeOH) (50 mL), HCl gas was bubbled in gently via septum for 10 minutes, during which time the solution cleared. The mixture was stoppered and allowed to stir at room temperature. After 2 hours, gaseous HCl was again introduced for 10 minutes with vigorous stirring. The mixture was stoppered and allowed to stir overnight at room temperature. The reaction mixture was concentrated 80% in vacuo, leading to the formation of white precipitate. The product, diiodotyrosine methyl ester hydrochloride, was filtered, washed with dichloromethane and dried in vacuo overnight.

The N-succinamido derivative of diiodotyrosine methyl ester was prepared using a procedure similar to that described in Example 3.

NHS ester activation of the N-succinamido derivative and conjugation to G6PDH were carried out by a procedure similar to that described in Example 1.

EXAMPLE 5

Preparation of N-Acetyldiiodotyrosine and Conjugation to G6PDH

To a diiodotyrosine slurry (1 g) in absolute ethanol (70 mL), acetic anhydride (70 mL) was added slowly with stirring and the reaction mixture was allowed to stir overnight at room temperature. Solvent was removed in vacuo from the clear reaction mixture, resulting in precipitation of a white diacetyl product.

To this diacetyl product, 0.1N NaOH (100 mL) was added and the reaction was stirred for 2 hours at room temperature, during which time the product was dislodged from the container walls manually to form a suspension. To this suspension, 10N NaOH (100 mL) was added and the suspension was stirred for an additional 2 hours. The monoacetyl product was purified by centrifugation and repeated washings of the pellet with deionized waster. A final purification was achieved by crystallization of the product from an 80% ethanol solution with 2N HCl. The product, N-acetyldiiodotyrosine, was filtered and dried in vacuo overnight.

NHS ester activation of N-acetyldiiodotyrosine and conjugation to G6PDH were carried out by a procedure similar to that described in Example 1.

EXAMPLE 6

Preparation of 3,5-Diiodo-4-hydroxyphenoxyacetic Acid and Conjugation to G6PDH

To a bright orange solution of 2,6-diiodoquinone (Pfalz and Bauer) (1 g) in degassed methanol (300 mL) was added a 10% aqueous solution of sodium bisulfite (11.6 mL) with stirring at room temperature for 15 minutes. Solvent was removed in vacuo from the resultant yellow reaction mixture. The residue was dissolved in methanol and the insoluble inorganic salts were removed by filtration. The product, 2,6-diiodohydroquinone, was washed with cold deionized water and dried in vacuo overnight.

To 2,6-diiodohydroquinone (0.2 g) in pyridine (10 mL) was added benzoyl chloride (0.140 mg) and the reaction mixture was stirred at room temperature for 1 hour. Following solvent removal in vacuo, purification was achieved by extraction (equal volumes ethyl acetate (EtOAc):0.01N HCl), and preparative TLC (methylene chloride) of the concentrated (in vacuo) EtOAc phases. Both the desired monoester, 4-hydroxy-2,6-diiodophenyl benzoate (Rf 0.38) and the diester, 3,5-diiodo-4(phenylmethanoyloxy)phenyl benzoate (Rf 0.96), products were formed.

To 4-hydroxy-2,6-diiodophenyl benzoate (0.0584 g) in dry acetone (10 mL) in an inert argon environment, potassium carbonate (0.0862 mg) and methyl bromoacetate (0.160 mg) were added and the reaction mixture was stirred at room temperature for 1 hour. Following solvent removal in vacuo, purification of 2,6-diiodo-4-(methoxycarbonylmethoxy)phenyl benzoate was achieved by extraction (equal volumes EtOAc:0.01N HCl), and preparative TLC (methylene chloride) of the concentrated (in vacuo) EtOAc phases.

2,6-diiodo-4-(methoxycarbonylmethoxy)phenyl benzoate (0.0134 g) was deesterified by stirring for 1 hour at room temperature in 10% aqueous potassium carbonate/90% methanol (10 mLs). Following solvent removal in vacuo, purification of 3,5-diiodo-4-hydroxyphenoxyacetic acid was achieved by extraction (equal volumes EtOAc:0.01N HCl), and preparative TLC (94:5:1 methylenel chloride, methanol, trifluoroacetic acid) of the concentrated (in vacuo) EtOAc phases.

NHS ester activation of the 3,5-diiodo-4-hydroxyphenoxyacetate acid and conjugation to G6PDH were carried out by a procedure similar to that described in Example 1.

EXAMPLE 7

Preparation of N-thioacetyldiiodotyrosine and conjugation to G6PDH

To diiodotyrosine (0.1 g) dissolved in pyridine (10 mL) was added the NHS ester of methyldithioacetic acid (0.081 g) and the reaction mixture was stirred overnight at room temperature. Purification was by extraction (equal volumes ethylacetate (EtOAc):0.01N HCl), and preparative thin layer chromatography (TLC) (94:5:1 methylene chloride: methanol: acetic acid) of the concentrated (in vacuo) EtOAc phases.

To N-methyldithioacetyl diiodotyrosine (27 mg) dissolved in degassed $CH_3OH$ (9 mL) was added triethylamine (27 μl) followed by dithioerythritol (5.6 mg) dissolved in degassed $CH_3OH$ (564 μl). The mixture was stirred under argon for 15 minutes at room temperature, after which solvent was removed in vacuo and the product washed twice with $CH_3OH$. The resultant product, N-thioacetyl diiodotyrosine, was dried in vacuo an additional 30 minutes over KOH>.

Native G6PDH was dialyzed at 4° C. with 3 changes of buffer (55 mM Tris, pH8). The concentration of enzyme used was 8-12 mg/mL. To G6PDH (59 mg) at 4° C. was added the NHS ester of bromoacetic acid (5.5 mg). The NHS ester was added slowly in portions to achieve appropriate % deactivation. The resultant bromoacetyl BA-G6PDH (BA-G6PDH) was dialyzed with 3 changes of buffer (55 mM Tris, pH 8).

To BA-G6PDH (54 mg @ 4-5 mg/mL) at 4° C. was slowly added freshly prepared N-thioacetyl diiodotyrosine (27 mg dissolved in 900 μl DMF). Deactivation and inhibition were monitored with time. Maximum % inhibition was achieved after 4 hours reaction time, after which the enzyme conjugate was dialyzed with 3 changes of buffer (1 & 2: 55 mM Tris, pH8 and 3: 50 mM phosphate, 150 mM NaCl, pH 7).

EXAMPLE 8

Preparation of N-thioacetyldiiodotyrosine Methyl Ester and Conjugation to G6PDH Diiodotyrosine methyl ester hydrochloride was prepared from diiodotyrosine using a procedure similar to that described in Example 3. The N-thioacetyl derivative of diiodotyrosine methyl ester hydrochloride was prepared and conjugated to bromoacetyl G6PDH by a procedure similar to that described in Example 7.

EXAMPLE 9

Assay for Thyroid Compound

Reagents (1) Reagent I contained T4 specific antibody in antibody diluent: 9 mM nicotinamide dinucleotide (NAD), 9.5 mM Glucose-6-phosphate (G6P), 0.26 mM 8-anilinonaphthalene sulfonic acid (ANS) in a Tris pH 6.0 buffer. The T4 specific antibody was spiked into the antibody diluent at the dilutions indicated below in Table 1 to give optimal assay separations for the enzyme conjugate utilized. This assay separation is the difference in rate in signal units between each calibrator and the negative calibrator and the difference between each calibrator and the high concentration calibrator. The T4 specific antibody was prepared by standard hybrid cell technology of Kohler and Milstein, Nature (1975) 265:495–497. Reviews of monoclonal antibody techniques are found, for example, in "Lymphocyte Hybridomas," ed. Melchers, et al., Springer-Verlag (New York 1978), Nature (1977) 266:495, Science (1980) 208:692 and Methods of Enzymology (1981) 73 (part B): 3-46.and identified as 4D5. Briefly, an immunogen, namely T4-galacturonic acid-bovine serum albumin (BSA), was prepared by a procedure similar to that described in U.S. Pat. No. 4,040,907 at column 16, line 3, to column 17, line 23. The samples of the immunogen were injected into mice and, after a sufficient time, the mice were sacrificed and spleen cells obtained. The spleen cells were fused in the presence of polyethylene glycol with myeloma cell line NS-1 obtained from the American Type Culture Collection. The resulting cells, which included fused hybridomas, were allowed to grow in a selective medium, namely, hypoxanthine aminopterine thymidine (HAT), and the surviving immortalized cells were grown in such medium using limiting dilution conditions. The supernatants in the reaction containers were screened for a monoclonal antibody having the desired specificity. The monoclonal antibody (4D5) obtained was isolated and purified according to conventional techniques (see, for example, Kohler and Milstein, supra).

(2) Reagent II contained enzyme conjugate in enzyme diluent: 18.9 mM Glucose-6-phosphate in a Tris/Barbital pH 8.0 buffer. Enzyme conjugates were spiked into separate aliquots of the enzyme diluent at the appropriate dilutions to achieve equivalent substrate turnover per unit time (Δ A340/minute) with Reagent A containing no antibody. The enzyme conjugates employed were:

(A) enzyme conjugate in accordance with the present invention prepared as described in Example 1 and (B) for purposes of comparison not in accordance with the present invention an enzyme conjugate prepared as described in U.S. Pat. No. 4,847,195, namely, a conjugate of 4'-(4-hydroxy- 3,5-diiodophenoxy)-3',5'-diiodobenzoic acid and G6PDH (T4-G6PDH conjugate).

(3) Calibrators were prepared at 0, 2, 4, 8, 12, and 20 μg/dL thyroxine in thyroxine-free serum.

Automated analyzer

Roche Mira S

Protocol

1. Incubate 4 μl calibrator or patient sample with 55 μl distilled water and 150 μl Reagent I for 5 minutes (37° C.).
2. Add 75 μl Reagent II, containing enzyme conjugate, and 20 μl distilled water, and observe enzyme rate at 340 nm (37° C.) for 125 sec.

Patient samples containing serum binding proteins that interfere with T4 quantitation using the T4-G6PDH conjugate (column B in Table 1) were run with the enzyme conjugates in accordance with the present invention (column A in Table 1). These patient samples were returned from the field as discrepant samples using the EMIT T4 assay sold by Syva Company (EMIT is a trademark of Syva Company) and are identified in Table 1 by their sample identification (ID) number. Also, for purposes of comparison these patient samples were analyzed using an IMX (registered trademark of Abbott Laboratories, Abbott Park, Ill.) thyroxine assay (lot number 53072Q100) according to the manufacturer's instructions (C). The results are summarized below in Table 1.

TABLE I

| | ASSAY FOR T4 | | |
| --- | --- | --- | --- |
| | Total T4 (μg/dL) | | |
| Sample ID | A1 | B2 | C3 |
| 9579 | 9.3 | 0.92 | 10.0 |
| 11677 | 3.4 | 0.65 | 5.1 |
| 11178 | 9.0 | 4.57 | 10.5 |
| 12431 | 6.9 | 2.19 | 7.6 |
| 14021 | 6.1 | 2.52 | 6.8 |
| 14878 | 15.2 | <0 | 14.4 |

1 - enzyme conjugate in accordance with the present invention prepared as described in Example 1.
2 - for purposes of comparison not in accordance with the present invention, an enzyme conjugate prepared as described in U.S. Pat. No. 4,847,195, namely, a conjugate of 4'-(4-hydroxy-3,5-diiodophenoxy)-3', 5'-diiodobenzoic acid and G6PDH (T4-G6PDH conjugate).
3 - for purposes of comparison, IMX (registered trademark of Abbott Laboratories, Abbott Park, Illinois) thyroxine assay (lot number 53072Q100) used according to the manufacturer's instructions.

The conjugate of Example 1 was also utilized in a similar protocol as described above for a T-Uptake assay. The interference seen with the use of the enzyme conjugate in accordance with U.S. Pat. No. 4,847,195, namely, conjugate B above, was not observed with the conjugate of the invention. The results obtained with the conjugate of the present invention were similar to the results obtained using an Abbott IMX assay for T-Uptake used in accordance with the manufacturer's instructions.

The above assay was repeated using in place of the conjugate of Example 1 the conjugates of Examples 2-8, respectively. The following is a rank of the conjugates based on their comparative performance in the above assay protocol: (1) Example 1, (2) Example 3, (3) Example 4, (4) Example 2, (5) Example 5, (6) Example 6, (7) Example 8 and (8) Example 7.

The results of the foregoing example demonstrate that extremely low concentrations, as well as extremely small amounts of thyroxine can be detected by a method employing the thyroid analog-G6PDH conjugates of the present invention. The method is quite straightforward in requiring few manipulative steps. By combining the reagents in a buffered medium, and optionally incubating the mixture, followed by the addition of the enzyme substrates, a thyroid compound analyte can be determined by a spectrophotometric reading over a short period of time. The system allows for automation, so that samples and reagents can be mixed automatically and read. The thyroid analog-G6PDH conjugates offer a distinct advantage over conjugates having more than one phenyl ring that contains a hydroxyl or substituted hydroxyl substituent and one or two iodine atoms in an ortho relationship to the hydroxyl substituent on the phenyl ring. Compounds possessing more than one such phenyl ring, when used in the above assay, did not give meaningful results as indicated by the descrepant samples sent from the field.

Although the foregoing invention has been described in some detail by way of illustration and example for purposes of clarity of understanding, it will be obvious that certain changes and modifications may be practiced within the scope of the appended claims.

We claim:

1. In a method analyzing for the presence or amount of a thyroid compound in a medium suspected of containing a thyroid compound, said method comprising the steps of (a) combining said medium with an antibody specific for said compound and an enzyme conjugate comprising an enzyme bound to a polyiodothyronine analog and (b) determining the effect of said assay medium on the activity of said enzyme wherein the activity of said enzyme is related to the presence or amount of said thyroid compound in said medium, the improvement which comprises said polyiodothyronine analog being a thyroid analog that is a compound having only one phenyl ring that contains a hydroxyl substituent or a substituted hydroxyl substituent and one or two substituents, independently selected from the group consisting of iodine and iodine surrogates that are isoteric with iodine, in an ortho relationship to the hydroxyl substituent on the phenyl ring, said phenyl ring being bound to said enzyme by means of a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxyl substituent or the substituted hydroxyl substituent and that the atom directly attached to the phenyl ring bearing the hydroxyl substituent or the substituted hydroxyl substituent is carbon, nitrogen or sulfur.

2. The method of claim 1 wherein said substituents are iodine or t-butyl.

3. The method of claim 1 wherein said substituents are iodine.

4. The method of claim 1 wherein said method is a homogeneous assay.

5. The method of claim 1 wherein said enzyme is a dehydrogenase.

6. The method of claim 1 wherein said enzyme is glucose-6-phosphate dehydrogenase.

7. In a method analyzing for the presence or amount of a thyroid compound in a medium suspected of containing a thyroid compound, said method comprising the steps of (a) combining said medium with an antibody specific for said thyroid compound and an enzyme conjugate comprising an enzyme bound to a polyiodothyronine analog and (b) determining the effect of said assay medium on the activity of said enzyme wherein the activity of said enzyme is related to the presence or amount of said thyroid compound in said medium, the improvement which comprises said antibody being raised against an immunogenic conjugate comprising an immunogenic carrier bound to a thyroid analog that is a compound having only one phenyl ring that contains a hydroxyl substituent or a substituent hydroxyl substituent and one or two substituents, independently selected from the group consisting of iodine and iodine surrogates that are isoteric with iodine, in an ortho relationship to the hydroxyl substituent on the phenyl ring, said phenyl ring being bound to said enzyme by means of a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxyl substituent or the substituted hydroxyl substituent and that the atom directly attached to the phenyl ring bearing the hydroxyl substituent or the substituted hydroxyl substituent is carbon, nitrogen or sulfur.

8. The method of claim 7 wherein said substituents are independently iodine or t-butyl.

9. The method of claim 7 wherein said substituents are iodine.

10. The method of claim 7 wherein said method is a homogeneous assay.

11. The method of claim 7 wherein said enzyme is a dehydrogenase.

12. The method of claim 7 wherein said enzyme is glucose-6-phosphate dehydrogenase.

13. A method for detecting the presence or amount of a thyroid compound in a sample suspected of containing the same, which method comprises:
   (a) combining in an aqueous medium the sample, an antibody for said thyroid compound, and a compound of the formula;

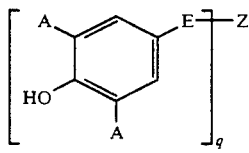

(1)

wherein:
A is independently iodine, t-butyl or hydrogen, wherein at least one of A is other than hydrogen
E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxy group and that the atom directly attached to the phenyl ring bearing the hydroxy group is carbon, nitrogen or sulfur,
Z is an enzyme, and
q is a number from 1 to the molecular weight of Z divided by 5000, and
   (b) determining the enzyme activity of said medium, the enzyme activity being related to the presence or amount of said thyroid compound is said sample.

14. The method of claim 13 wherein A is independently iodine or hydrogen.

15. The method of claim 13 wherein A is iodine.

16. The method of claim 13 wherein Z in said compound is a dehydrogenase.

17. The method of claim 13 wherein Z in said compound is glucose-6-phosphate dehydrogenase.

18. The method of claim 13 wherein said chain in said compound is 2 to 8 atoms in length, said atoms being selected from the group consisting of carbon, oxygen and nitrogen.

19. The method of claim 13 wherein said chain in said compound has the formula:

wherein R is independently selected from the group consisting of hydrogen, alkyl of 1 to 5 carbon atoms, $N(R')_2$ wherein $R'$ are independently selected from the group consisting of hydrogen and alkyl of 1 to 5 carbon atoms, wherein one or more of the carbon atoms in R and/or $R'$ may be substituted with carbon (C), chlorine, bromine, fluorine, oxygen (O), nitrogen (N), sulfur (S), or phosphorus (P), wherein the O, N, S, or P, if present, are bound to carbon or one or more of each other or to hydrogen to form a functional group,
   a is 0,
   b is 1 to 4,
   c is 1 or 2,
   d is 0 or 1,
   e is 1 or 2,
   f is 0 or 1
with the proviso that $a+b+c+d+e$ not be greater than 7, and
X is independently selected from the group consisting of oxygen, sulfur and NH.

20. The method of claim 13 wherein said chain in said compound is independently selected from the group consisting of

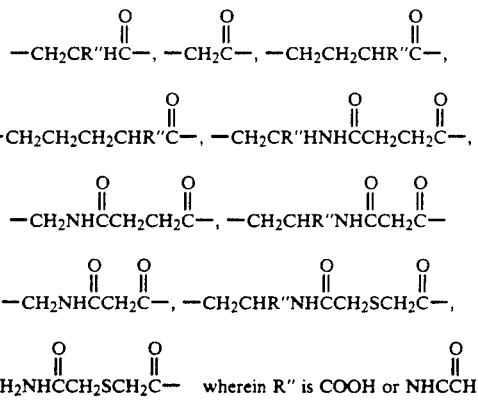

wherein $R''$ is COOH or $NHCCH_3$.

21. The method of claim 13, wherein said compound is

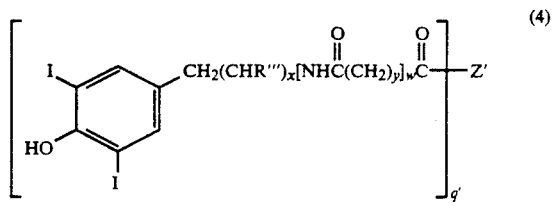

(4)

wherein
$R'''$ is selected from the group consisting of hydrogen, carboxy,
carboxy alkyl ester of 1 to 5 carbon atoms and $NHD'$, wherein D is selected from the group consisting of hydrogen, and alkyl carbonyl of 1 to 5 carbon atoms, Z' is glucose-6-phosphate dehydrogenase, q' is 1 to 10, and x is 0 or 1 y is 1 or 2 w is 0 or 1.

22. The method of claim 21 wherein in the compound w is 0 and R''' is hydrogen.

23. The method of claim 21 wherein in the compound w is 1, y is 2 and R''' is hydrogen.

24. The method of claim 21 wherein in the compound x is 1, y is 2, w is 1 and R''' is $CO_2CH_3$.

25. The method of claim 21 wherein in the compound x and w are 0.

26. The method of claim 21 wherein said method is a homogeneous assay.

27. The method of claim 13 wherein the atoms of said chain do not include a phenyl ring.

28. In an enzyme immunoassay method for detecting the presence or amount of a thyroid compound in a sample suspected of containing the same, said method comprising the steps of combining said sample with a conjugate of an enzyme and a polyiodothyronine analog and an antibody capable of binding to said thyroid compound and said polyiodothyronine analog and measuring the enzyme activity of said enzyme, the enzyme activity being related to the presence or amount of said thyroid compound in said sample, the improvement which comprises employing as the conjugate a compound of the formula:

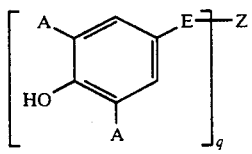

(1)

wherein:

A is independently iodine, t-butyl or hydrogen, wherein at least one of A is other than hydrogen, E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxy group and that the atom directly attached to the phenyl ring bearing the hydroxy group is carbon, nitrogen or sulfur, Z is an enzyme, and q is a number from 1 to the molecular weight of Z divided by 5000.

29. The method of claim 28 wherein A is independently iodine or hydrogen.

30. The method of claim 28 wherein A is iodine.

31. The method of claim 28 wherein said method is a homogeneous assay.

32. The method of claim 28 wherein the atoms of said chain do not include a phenyl ring.

33. A method for detecting the presence or amount of a thyroid compound in a sample suspected of containing the same, which method comprises:

(a) combining in an aqueous medium the sample, a conjugate of a thyroid analog and an enzyme, and an antibody raised against a compound of the formula:

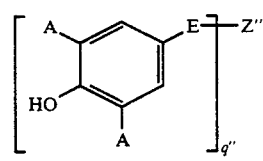

(2)

wherein:

A is independently iodine, t-butyl or hydrogen, wherein at least one of A is other than hydrogen, E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxy group and that the atom directly attached to the phenyl ring bearing the hydroxy group is carbon, nitrogen or sulfur, Z'' is an immunogenic carrier, and q'' is a number from 1 to the molecular weight of Z divided by 5000, and (b) determining the enzyme activity of said medium, the enzyme activity thereof being related to the presence or amount of said thyroid compound in said sample.

34. The method of claim 33 wherein A is independently iodine or hydrogen.

35. The method of claim 33 wherein A is iodine.

36. The method of claim 33 wherein Z'' in said compound is selected from the group consisting of immunogenic proteins and immunogenic particles.

37. The method of claim 33 wherein the enzyme in said compound is a dehydrogenase.

38. The method of claim 33 wherein the enzyme in said compound is glucose-6-phosphate dehydrogenase.

39. The method of claim 13 wherein said chain in said compound is 1 to 5 atoms in length, said atoms being selected from the group consisting of carbon, oxygen and nitrogen.

40. The method of claim 33 wherein said chain in said compound has the formula:

wherein R is independently selected from the group consisting of hydrogen, alkyl of 1 to 5 carbon atoms, $N(R')_2$ wherein R' are independently selected from the group consisting of hydrogen and alkyl of 1 to 5 carbon atoms, wherein one or more of the carbon atoms may be substituted with carbon (C), chlorine, bromine, fluorine, oxygen (O), nitrogen (N), sulfur (S), phosphorus (P), wherein the O, N, S, or P, if present, are bound to carbon or one or more of each other or to hydrogen to form a functional group, a is 0, b is 1 to 4, c is 1 or 2, d is 0 or 1, e is 1 or 2, 0 or 1 f is 0 or 1 with the proviso that $a+b+c+d+e$ not be greater than 7, and

X is independently selected from the group consisting of oxygen, sulfur and NH.

41. The method of claim 33 wherein said chain in said compound is independently selected from the group consisting of

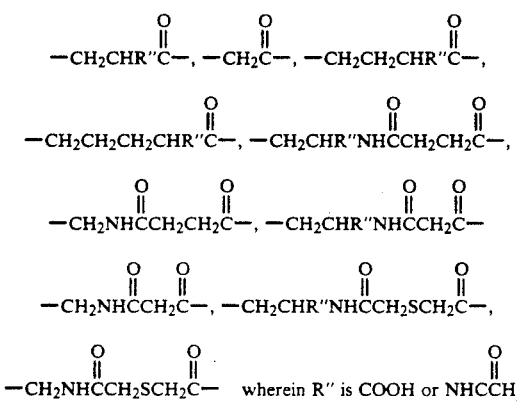

wherein R'' is COOH or NHCCH$_3$.

42. The method of claim 33, wherein said compound is

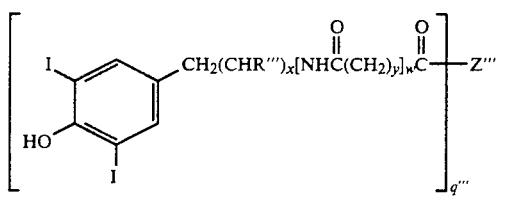

wherein:
R''' is selected from the group consisting of hydrogen, carboxy, carboxy alkyl ester of 1 to 5 carbon atoms and NHD', wherein D is selected from the group consisting of hydrogen and alkyl carbonyl of 1 to 5 carbon atoms
Z''' is an albumin or a gammaglobulin,
q''' is 1 to 10,
x is 0 or 1
y is 1 or 2 and
w is 0 or 1.

43. The method of claim 42 wherein in the compound w is 0 and R''' is hydrogen.

44. The method of claim 42 wherein in the compound w is 1, y is 2 and R''' is hydrogen.

45. The method of claim 42 wherein said method is a homogeneous assay.

46. The method of claim 33 wherein the atoms of said chain do not include a phenyl ring.

47. A kit comprising in packaged combination:
(a) a compound of the formula:

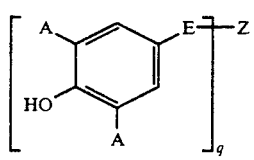

wherein:
A is independently iodine, t-butyl or hydrogen, wherein at least one of A is other than hydrogen,
E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxy group and that the atom directly attached to the phenyl ring bearing the hydroxy group is carbon, nitrogen or sulfur,
Z is an enzyme, and
q is a number from 1 to the molecular weight of Z divided by 5000, and
(b) an antibody specific for a thyroid compound.

48. The kit of claim 47 wherein A is independently iodine or hydrogen.

49. The kit of claim 47 wherein A is iodine.

50. The kit of claim 47 wherein said compound is selected from the group consisting of:

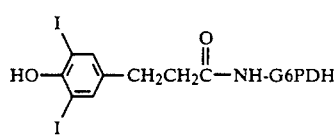

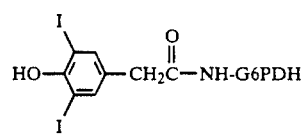

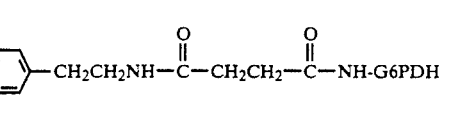

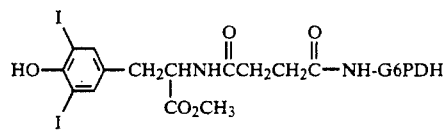

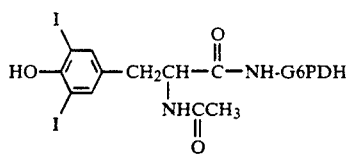

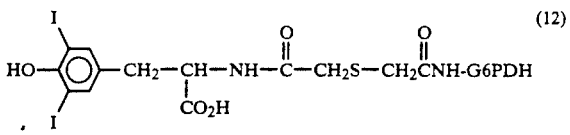

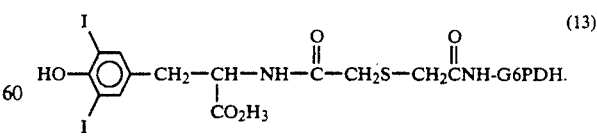

51. The kit of claim 47 wherein the atoms of said chain of said compound do not include a phenyl ring.

52. A kit comprising in packaged combination:
(a) an antibody raised against a compound of the formula:

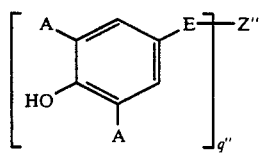

(2)

wherein:
A is independently iodine, t-butyl or hydrogen, wherein at least one of A is other than hydrogen,
E is a bond or a linking group having a chain having a length of 1 to 10 atoms, said atoms being selected from the group consisting of carbon, oxygen, nitrogen, sulfur and phosphorus, with the proviso that the atoms of said chain not include a phenyl ring within at least 2 atoms of the phenyl ring bearing the hydroxy group and that the atom directly attached to the phenyl ring bearing the hydroxy group is carbon, nitrogen or sulfur,
Z" is an immunogenic carrier, and
q" is a number from 1 to the molecular weight of Z divided by 5000, and
  (b) conjugate of a thyroid analog and an enzyme.
  53. The kit of claim 52 wherein A is independently iodine or hydrogen.
  54. The kit of claim 52 wherein A is iodine.
  55. The kit of claim 52 wherein the atoms of said chain of said compound do not include a phenyl ring.

* * * * *